(12) United States Patent
Beyer

(10) Patent No.: US 12,409,051 B2
(45) Date of Patent: *Sep. 9, 2025

(54) SPINE CAGE HOLDER

(71) Applicant: Neo Medical SA, Villette (CH)

(72) Inventor: Morten Beyer, Rødkærsbro (DK)

(73) Assignee: Neo Medical SA, Villette (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/191,383

(22) Filed: Mar. 28, 2023

(65) Prior Publication Data

US 2023/0225882 A1 Jul. 20, 2023

Related U.S. Application Data

(63) Continuation of application No. 16/969,212, filed as application No. PCT/IB2019/051520 on Feb. 26, 2019, now Pat. No. 11,628,070.

(30) Foreign Application Priority Data

Feb. 26, 2018 (WO) .................. PCT/IB2018/051188

(51) Int. Cl.
*A61F 2/46* (2006.01)
*A61F 2/44* (2006.01)

(52) U.S. Cl.
CPC .......... *A61F 2/4611* (2013.01); *A61F 2/4455* (2013.01); *A61F 2002/4681* (2013.01); *A61F 2310/00017* (2013.01); *A61F 2310/00023* (2013.01); *A61F 2310/00047* (2013.01); *A61F 2310/00107* (2013.01); *A61F 2310/00131* (2013.01); *A61F 2310/00149* (2013.01)

(58) Field of Classification Search
CPC ........ A61F 2/46; A61F 2/4603; A61F 2/4611; A61F 2002/4625; A61F 2002/4627; A61F 2002/4629

See application file for complete search history.

(56) References Cited

U.S. PATENT DOCUMENTS

| | | | |
|---|---|---|---|
| 5,913,860 A | 6/1999 | Scholl | |
| 8,088,163 B1 | 1/2012 | Kleiner | |
| 9,107,768 B2 * | 8/2015 | Schell | A61F 2/4455 |
| 9,226,835 B2 * | 1/2016 | Schell | A61B 17/7064 |
| 9,265,622 B2 * | 2/2016 | Schell | A61F 2/447 |
| 9,566,170 B2 * | 2/2017 | Schell | A61B 17/1757 |

(Continued)

FOREIGN PATENT DOCUMENTS

| | | |
|---|---|---|
| CN | 105662662 A | 6/2016 |
| EP | 1124510 A2 | 8/2001 |

(Continued)

OTHER PUBLICATIONS

International Search Report dated Jun. 11, 2019 for Application N° PCT/IB2019/051520.

(Continued)

*Primary Examiner* — Eric S Gibson
(74) *Attorney, Agent, or Firm* — NIXON & VANDERHYE

(57) ABSTRACT

A cage holder includes an elongated body having a proximal end and a distal end, the elongated body extending from the proximal end to the distal end. The cage holder further includes means for transferring energy centrally from the proximal end to the distal end through the elongated body.

15 Claims, 6 Drawing Sheets

(56) References Cited

U.S. PATENT DOCUMENTS

| | | | | |
|---|---|---|---|---|
| 11,628,070 | B2* | 4/2023 | Beyer | A61F 2/4455 623/17.11 |
| 2002/0016592 | A1* | 2/2002 | Branch | A61F 2/4611 606/279 |
| 2005/0240197 | A1 | 10/2005 | Kmiec | |
| 2010/0298941 | A1* | 11/2010 | Hes | A61F 2/4425 623/17.16 |
| 2011/0230965 | A1* | 9/2011 | Schell | A61B 17/7064 606/86 A |
| 2013/0226186 | A1* | 8/2013 | Burgi | A61F 2/4609 606/91 |
| 2014/0194993 | A1* | 7/2014 | Schell | A61B 17/1757 623/17.16 |
| 2014/0214164 | A1* | 7/2014 | Schell | A61F 2/4611 623/17.11 |
| 2014/0214165 | A1* | 7/2014 | Schell | A61F 2/4455 623/17.11 |
| 2015/0045892 | A1* | 2/2015 | Lynn | A61B 17/1671 623/17.16 |
| 2015/0238327 | A1* | 8/2015 | Cheng | A61F 2/447 623/17.16 |
| 2016/0135963 | A1* | 5/2016 | Kerboul | A61F 2/4609 606/91 |
| 2016/0235448 | A1* | 8/2016 | Seex | A61B 17/808 |
| 2016/0374825 | A1 | 12/2016 | Kleiner | |
| 2017/0042696 | A1 | 2/2017 | Larsson | |
| 2017/0100260 | A1* | 4/2017 | Duffield | A61F 2/4611 |
| 2017/0340358 | A1* | 11/2017 | Bullard | A61B 17/1757 |
| 2019/0374350 | A1* | 12/2019 | Milz | B25B 23/1427 |
| 2020/0352739 | A1* | 11/2020 | Ouidja | A61F 2/30749 |
| 2020/0405504 | A1* | 12/2020 | Beyer | A61F 2/4455 |
| 2021/0015630 | A1* | 1/2021 | Wall | A61F 2/4603 |
| 2021/0393408 | A1* | 12/2021 | Ginn | A61F 2/4611 |
| 2021/0393409 | A1* | 12/2021 | Ginn | A61B 6/032 |
| 2022/0031472 | A1* | 2/2022 | Bruffey | A61F 2/4455 |
| 2022/0151800 | A1* | 5/2022 | Huh | A61F 2/4611 |
| 2023/0225882 | A1* | 7/2023 | Beyer | A61F 2/4455 623/17.11 |

FOREIGN PATENT DOCUMENTS

| | | | | |
|---|---|---|---|---|
| JP | 2016511082 A | 4/2016 | | |
| WO | WO-2014088521 A2 * | 6/2014 | | A61F 2/442 |
| WO | 2014/159739 A1 | 10/2014 | | |
| WO | 2014159027 A1 | 10/2014 | | |
| WO | 2015/162514 A1 | 10/2015 | | |

OTHER PUBLICATIONS

Written Opinion of the ISA dated Jun. 11, 2019 for Application N° PCT/IB2019/051520.

Office Action, issued in Japanese Patent Application No. 2020-543280 dated Feb. 28, 2023.

Office Action, issued in Japanese Patent Application No. 2020-543280 dated Oct. 17, 2023.

* cited by examiner

SPINE CAGE HOLDER

CROSS-REFERENCE TO RELATED APPLICATIONS

This application is a continuation application of U.S. patent application Ser. No. 16/969,212 filed on Aug. 12, 2020, which is the U.S. national phase of International Application No. PCT/IB2019/051520 filed on Feb. 26, 2019, which designated the U.S. and claims priority to international patent application PCT/IB2018/051188 filed on Feb. 26, 2018, the entire contents of each of which are hereby incorporated herein by reference.

FIELD OF THE INVENTION

The present invention concerns a cage holder and more particularly a spine cage holder. The device can be used for handling or manipulating, for example, a spine cage used for spinal fusion between two or more vertebrae of the spine.

BACKGROUND

During the insertion or placement of a spine cage between vertebrae of a patient it is often necessary to force the cage into a desired position between vertebrae thus requiring a force, such as a mechanical force, to be applied by for example hammering on the end of a cage holder to which a spinal cage is attached.

Known cage holders require repeated application of such a force to be applied to the cage holder to achieve a correct placement or positioning of the spine cage and thus complicates the surgical procedure or increases the risk of injury to the surgeon or patient.

WO2015162514 discloses an example of a spine cage.

SUMMARY

The goal of the present invention is to provide a cage holder that overcomes the above-mentioned inconvenience. In particular, a goal of the present invention is to assure that repeated application of such a force is avoided or at least minimized.

The present invention is thus a cage holder including an elongated body comprising a proximal end and a distal end, the elongated body extending from the proximal end to the distal end; and means for transferring energy centrally from the proximal end to the distal end through the elongated body.

The means for transferring energy centrally can be at least partially enclosed by the elongated body (3).

The cage holder according to the present invention advantageously includes means for transferring energy centrally from a proximal end to a distal end through the cage holder. This permits mechanical energy to be channeled through the core of the cage holder and guided directly to the cage for an efficient transfer of energy thus assuring that a repeated application of a force is not required or at least minimized.

Other advantageous features can be found in the dependent claims.

According to an aspect of the present disclosure, the means for transferring energy is configured to transfer energy centrally through the cage holder in a longitudinal direction of the cage holder.

According to another aspect of the present disclosure, the means for transferring energy is configured to transfer energy centrally through the cage holder in a longitudinal direction of the cage holder from an outer extremity of the proximal end of the cage holder to an outer extremity of the distal end of the cage holder.

According to another aspect of the present disclosure, the means for transferring energy centrally includes a cage holding or cage attachment means at a distal end.

According to an aspect of the present disclosure, the means for transferring energy centrally includes a member extending from the proximal end to the distal end of the elongated body, the member comprising or consisting of a first material and the elongated body comprising or consisting of a second material different to the first material.

According to an aspect of the present disclosure, the first material has a higher material density than the second material.

According to another aspect of the present disclosure, the member has a higher rigidity or a lower flexibility than the elongated body.

According to another aspect of the present disclosure, the means for transferring energy centrally includes a tube extending from the proximal end to the distal end of the elongated body.

According to another aspect of the present disclosure, the means for transferring energy centrally includes a tube extending from the proximal end of the cage holder to the distal end of the cage holder.

According to another aspect of the present disclosure, the tube extends from an outer extremity of the proximal end of the cage holder to an outer extremity of the distal end of the cage holder.

According to another aspect of the present disclosure, the elongated body delimits a passage in which the tube is located and/or held therein.

According to another aspect of the present disclosure, the passage extends from an outer extremity of the proximal end of the elongated body to an outer extremity of the distal end of the elongated body.

According to another aspect of the present disclosure, the tube is or defines a hollow tube; or the tube is a non-hollow solid tube or solid rod.

According to another aspect of the present disclosure, an external wall of the tube is located at a distance of at least 0.1 mm from the central longitudinal axis of the cage holder.

According to another aspect of the present disclosure, an external wall of the tube is located at a distance of between 0.5 mm and 5 mm from a central longitudinal axis of the cage holder.

According to another aspect of the present disclosure, the central longitudinal axis of the cage holder is located at a geometric center or center of symmetry of the cage holder and/or the elongated body.

According to another aspect of the present disclosure, the means for transferring energy centrally from the proximal end to the distal end through the elongated body further includes an elongated shaft removably held in the cage holder.

According to another aspect of the present disclosure, the elongated shaft is configured to movably slide within the cage holder from an outer extremity of the proximal end of the cage holder to an outer extremity of the distal end of the cage holder.

According to another aspect of the present disclosure, the elongated shaft is configured to be received by the tube; or is removably held by the tube.

According to another aspect of the present disclosure, the elongated shaft is configured to movably slide within the tube from an outer extremity of a proximal end of the tube to an outer extremity of a distal end of the tube.

According to another aspect of the present disclosure, the elongated shaft is a solid rod or a hollow rod or shaft.

According to another aspect of the present disclosure, the elongated shaft includes a knob at a first end.

According to another aspect of the present disclosure, the elongated shaft includes a cage holding or cage attachment means at a second end.

According to another aspect of the present disclosure, the distal end of the cage holder is configured to hold or attach a spinal cage.

According to another aspect of the present disclosure, the elongated body includes a handle and the proximal end of the elongated body is located at the end of the handle.

According to another aspect of the present disclosure, the cage holder is a spine cage holder.

According to another aspect of the present disclosure, the means for transferring energy centrally is configured to transfer mechanical energy.

According to another aspect of the present disclosure, said means is configured to transfer energy centrally from the proximal end to the distal end of the elongated body and centrally through the full length of the elongated body.

According to another aspect of the present disclosure, the elongated body comprises or consist of a plastic; and the means for transferring energy centrally from the proximal end to the distal end through the elongated body and/or the member comprises or consists of a metal, and/or the tube comprises or consists of a metal.

According to another aspect of the present disclosure, the elongated shaft comprises or consists of a metal.

The present invention also concerns a kit of instruments including the above-mentioned cage holder.

A BRIEF DESCRIPTION OF THE SEVERAL VIEWS OF THE DRAWINGS

The above object, features and other advantages of the present disclosure will be best understood from the following detailed description in conjunction with the accompanying drawings, in which:

FIGS. 1 to 11 show non-limiting and exemplary embodiments of the present disclosure.

FIG. 1 shows a cage holder according to an exemplary embodiment of the present disclosure.

FIG. 2 shows the cage holder of FIG. 1 in which a central shaft is fully inserted.

FIG. 3 shows a view of a proximal end of a cage holder of the present disclosure.

FIG. 4 shows the cage holder of FIG. 1 in which a central shaft is partially inserted.

FIG. 5 shows a shaft and knob at one end of a cage holder of the present disclosure, the being shaft is partially removed from a body of the cage holder.

FIG. 7 shows the extremity of a cage holder attached to a spine cage.

FIG. 8 shows a cage holder according to an exemplary embodiment of the present disclosure in which a central shaft is not present.

FIG. 9 shows a sectional view (along A1-A1 of FIG. 8) and top view of the cage holder of FIG. 8.

FIG. 10 shows a cage holder according to an exemplary embodiment of the present disclosure in which a central shaft is present.

FIG. 11 shows a sectional (along A-A of FIG. 10) and top view of the cage holder of FIG. 10.

Herein, identical reference numerals are used, where possible, to designate identical elements that are common to the Figures.

DETAILED DESCRIPTION OF THE SEVERAL EMBODIMENTS

Figure 1:
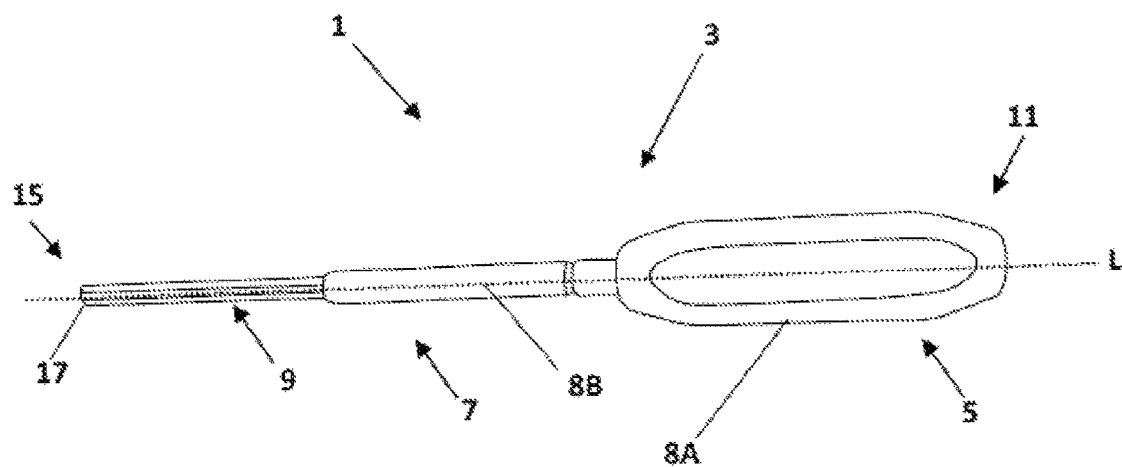
Figure 2:
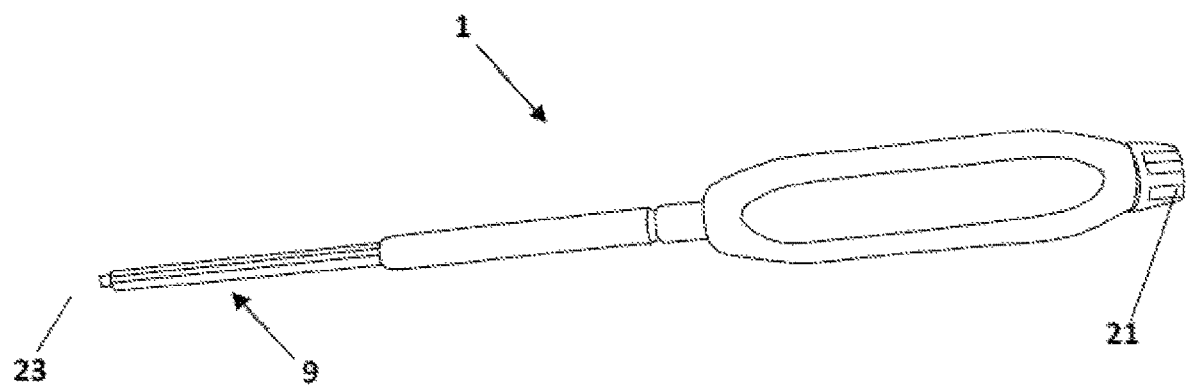

An exemplary cage holder 1 according to the present disclosure is shown, for example, in FIGS. 1 and 2.

The cage holder 1 includes an elongated body 3 comprising a proximal end 5 and a distal end 7, the elongated body 3 extending from the proximal end 5 to the distal end 7.

The elongated body 3 is for example made of, comprises or consists of a plastic or a polymer. The elongated body 3 is for example made of, comprises or consists of a polyvinyl chloride (PVC), polyethylene, a polyester, polycarbonate, polyetherether ketone (PEEK), ultra-high molecular weight polyethylene (UHMWPE) or polyarylamide.

The elongated body 3 may include, for example, a handle 8A and the proximal end 5 of the elongated body 3 is located at the end of the handle 8. The elongated body 3 may also include, for example, a sleeve 8B.

The cage holder 1 further includes means 9 for transferring energy centrally from the proximal end 5 to the distal end 7 and centrally through the full length of the elongated body. The means 9 for transferring energy is configured to transfer energy centrally through the cage holder 1 in a longitudinal direction of the cage holder 1. The means 9 for transferring energy is configured to transfer energy centrally through the cage holder in a longitudinal direction L (see FIG. 1) of the cage holder 1 from a proximal end 11 of the cage holder 1 to a distal end 15 of the cage holder 1. The longitudinal direction L extends in a direction running along or parallel to the length or extension of the elongated body 3.

The means 9 for transferring energy is, for example, partially or fully enclosed by the elongated body 3.

The means 9 for transferring energy is configured to transfer energy centrally through the cage holder 1 in the longitudinal direction L from an outer extremity of the proximal end 11 of the cage holder 1 to an outer extremity of the distal end 15 of the cage holder 1. As a result, this energy or force is efficiently transferred to a spine cage when located or attached at the extremity of the cage holder 1 to allow an easier insertion of the cage into a desired position between vertebrae.

The distal end 15 of the cage holder 1 is configured to hold or attach a spinal cage.

Figure 6A:
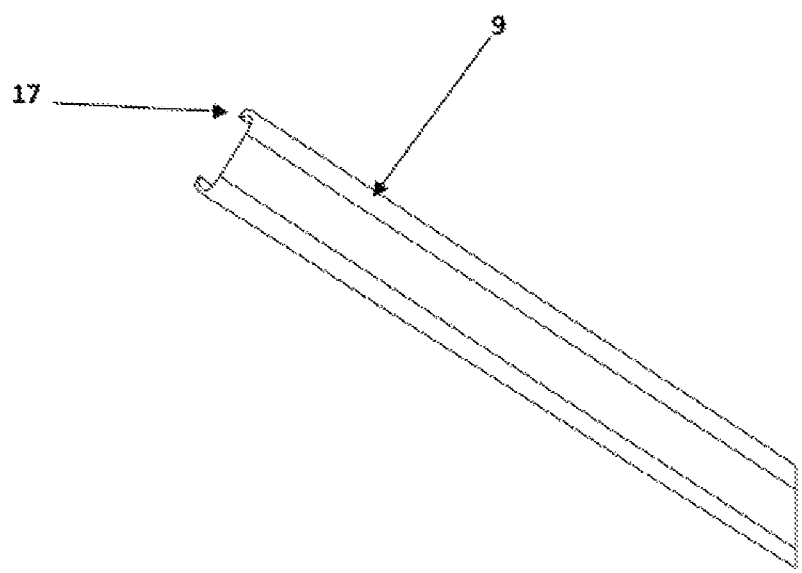
FIG. 6A shows an opposite extremity to that of FIG. 5 of a cage holder of the present disclosure.
Figure 6B:
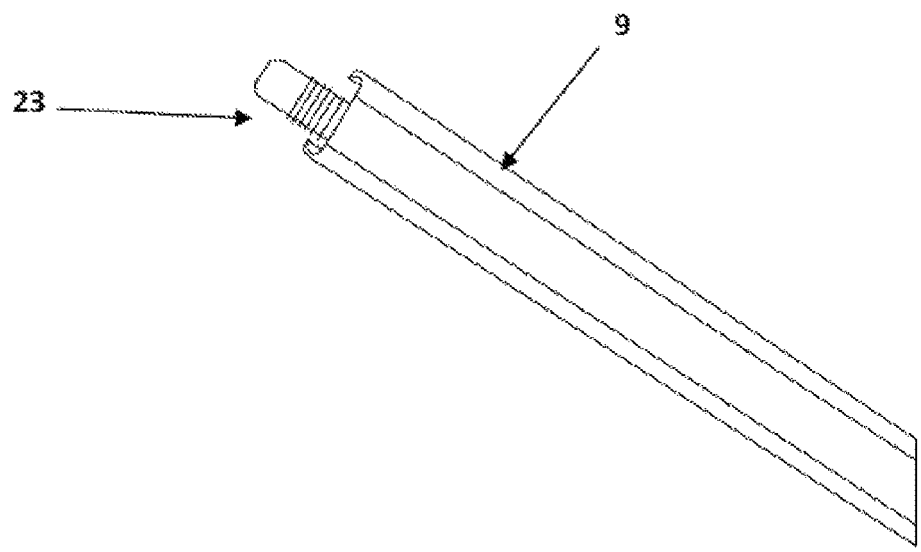
FIG. 6B shows the same extremity to that of FIG. 6A with the shaft of FIG. 5 being fully inserted.
Figure 7:
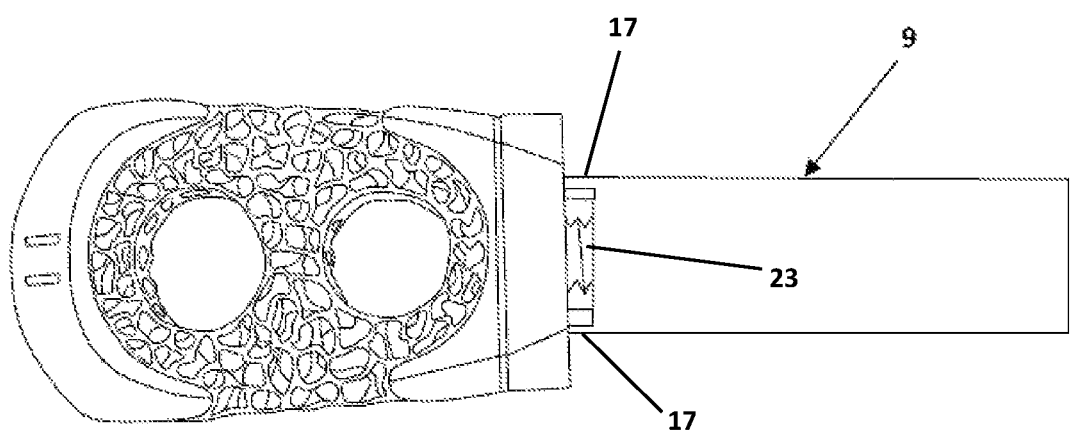
Figure 8:
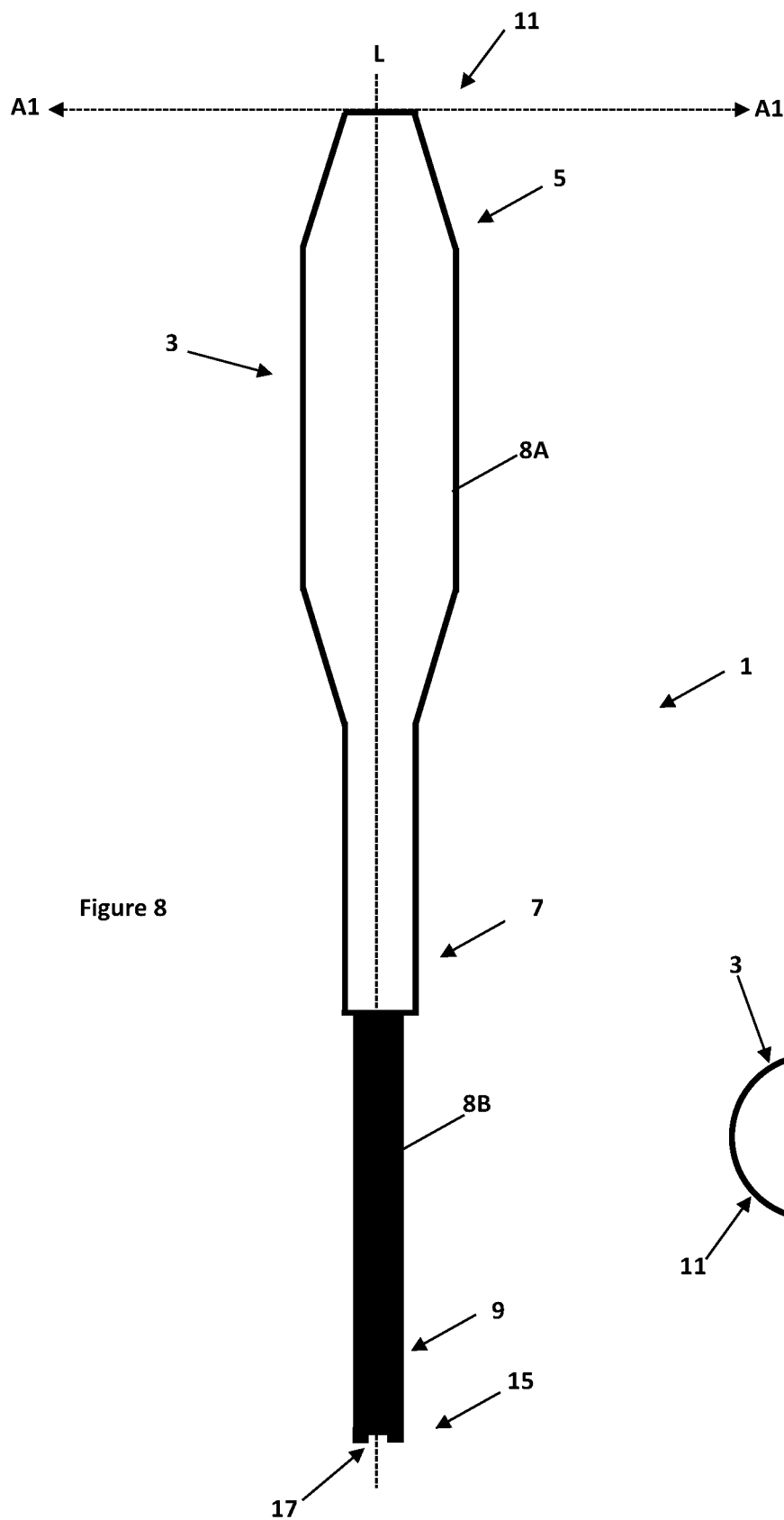
Figure 9:
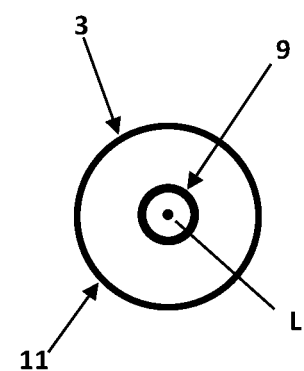
Figure 10:
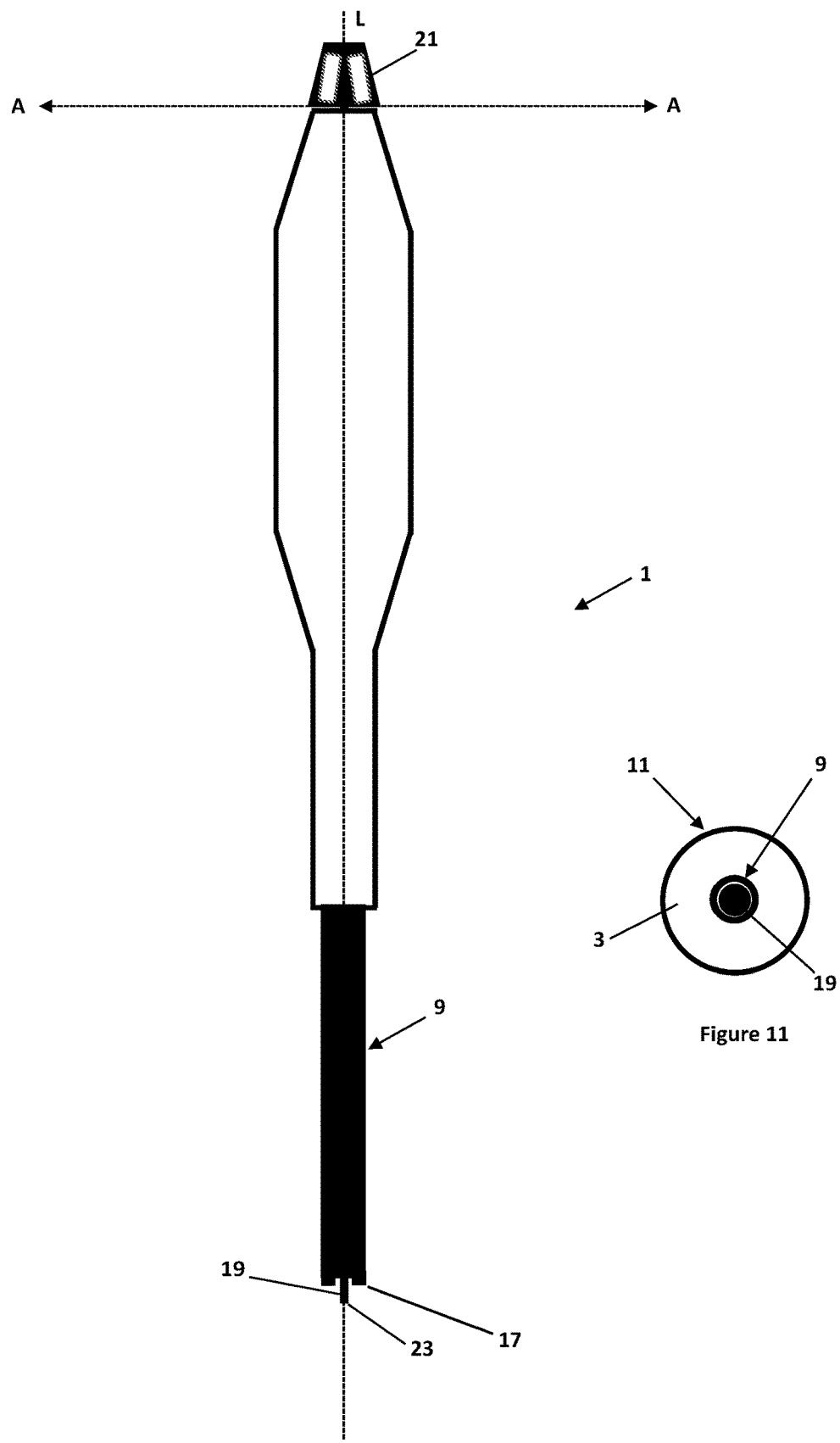
Figure 11:
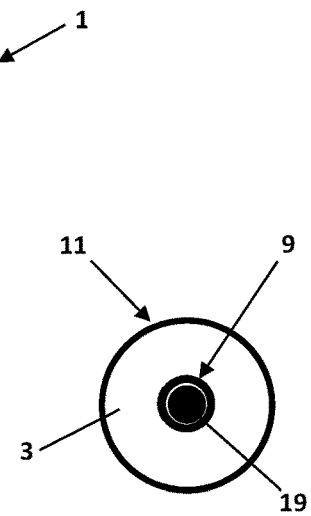

The means 9 for transferring energy centrally includes a cage holder, or a cage holding means or a cage attachment means 17 at the distal end (see in particular FIG. 6). The cage holding means or cage attachment means 17 can include, for example, one or more projections configured to, for example, cooperate with or be received by corresponding sockets of the cage (for example a spine cage, for example, as shown in FIG. 7). The cage can be, for example, attached by sliding or inserting the projections into the sockets of the cage.

The means 9 can be or include a core or central member located centrally in the cage holder and extending from the proximal end 11 to the distal end 15 of the cage holder 1. The core or central member is configured to transfer or guide energy centrally in the core of the cage holder 1 from the proximal end 11 to the distal end 15 of the cage holder 1. Mechanical energy applied at the proximal end 11 is channeled through the core of the cage holder to the proximal end. Dissipation or loss of the energy in non-central regions of the device is avoided permitting an optimum quantity of energy to be transferred to the cage.

The means 9 for transferring energy centrally includes a member 9 extending from the proximal end 5 to the distal end 7 of the elongated body 3. The member 9 comprises or consists of a first material and the elongated body 3 comprises or consists of a second material that, in a preferred embodiment, is different to the first material. Alternatively, the first and second material may also the same material.

The first material, may for example, have a higher material density than the second material. Alternatively or additionally, the member 9 may have a higher rigidity or a lower flexibility than the elongated body 3.

The member 9 or the means 9 for transferring energy centrally (or the core or central member) includes or is, for example, a tube 9. The tube 9 for is, for example, partially or fully enclosed by the elongated body 3.

The tube 9 extends from the proximal end 5 to the distal end 7 of the elongated body 3, and can extend beyond the distal end 7 of the body 3.

The tube 9 can extend from the proximal end 11 of the cage holder 1 to the distal end 15 of the cage holder 1. The tube 9 can extend from an outer extremity of the proximal end 11 of the cage holder 1 to an outer extremity of the distal end 15 of the cage holder 1.

Figure 3:
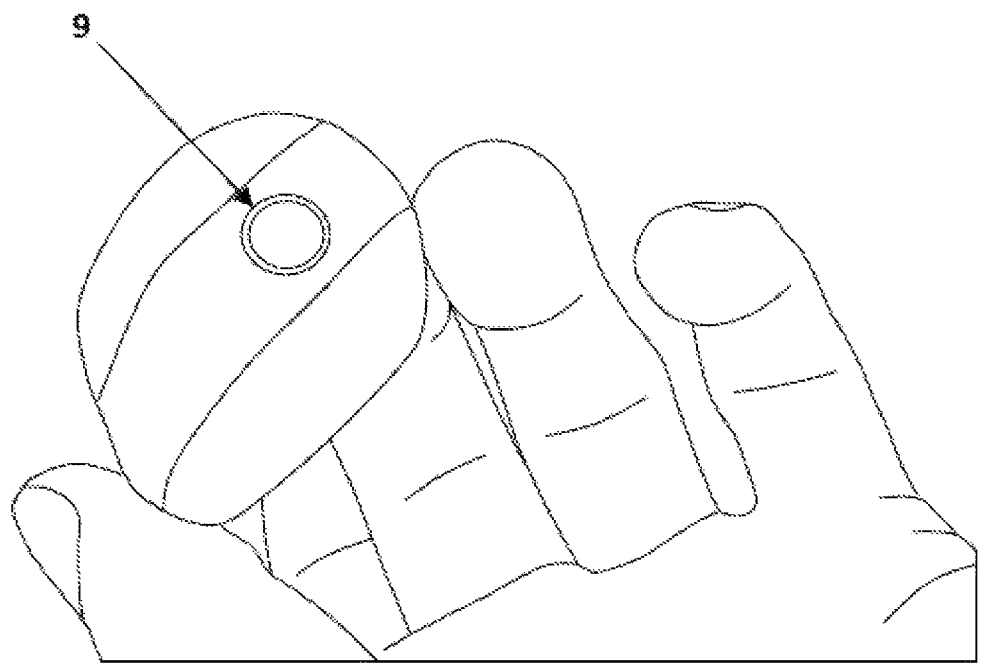

The elongated body 3 delimits a passage in which the tube is located and/or held therein (see for example FIG. 3). The passage extends from an outer extremity of the proximal end 5 of the elongated body 3 to an outer extremity of the distal end 7 of the elongated body 3.

The tube 9 can define a hollow tube. Alternatively, the tube can be a non-hollow solid tube or solid rod.

The tube 9 can be, for example, a metallic tube. The tube 9 can be made of, comprises or consists of, for example, stainless steel, or titanium, or tantalum, or platinum, or palladium or aluminum.

The tube 9 can be discontinuous in parts but extends continuously from the proximal end to the distal end for efficient energy transfer.

The tube 9 is preferably cylindric but may also have other shapes.

The tube 9 is preferably located in proximity to the central longitudinal axis L of the cage holder 1.

The tube 9, for example, encircles the central longitudinal axis L of the cage holder 1 or the central longitudinal axis L extends longitudinally through the tube.

An external wall of the tube is, for example, located at a distance of at least 0.1 mm from the central longitudinal axis L of the cage holder 1.

An external wall of the tube is, for example, located at a distance between 0.1 mm and 5 mm from a central longitudinal axis L of the cage holder 1.

The central longitudinal axis L of the cage holder 1 is located, for example, at a geometric center or center of symmetry of the cage holder 1 and/or the elongated body 3.

The external wall of the tube 9 directly contacts a wall of the elongated body 3 defining the passage in the elongated body 3.

The means 9 for transferring energy centrally may further include an elongated shaft 19 removably held in the cage holder 1. The elongated shaft 19 is configured to movably slide within the cage holder 1 from an outer extremity of the proximal end 11 of the cage holder to an outer extremity of the distal end 15 of the cage holder.

Figure 4:
Figure 5:
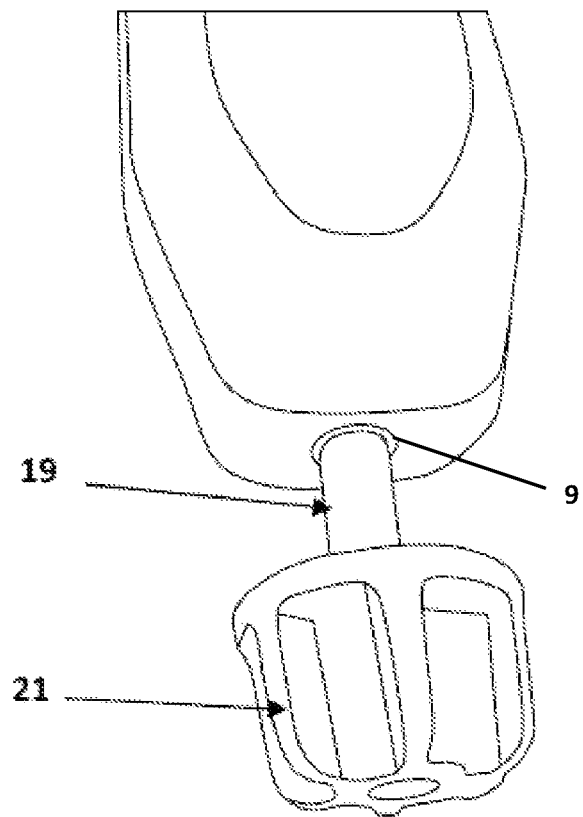

The cage holder 1 can thus further include the elongated shaft 19 or elongated central shaft 19 (see for example FIG. 4) configured to be received by the means 9 for transferring energy centrally, for example, the member or tube 9. In such a case the tube 9 is hollow.

The elongated shaft 19 is configured to be received by the tube (9) and is removably held by the tube 9. The elongated shaft 19 is configured to movably slide within the tube 9 from an outer extremity of a proximal end of the tube 9 to an outer extremity of a distal end of the tube 9.

The elongated shaft 19 can be for example a solid rod or a hollow shaft. The shaft 19 can be made of, comprises or consists of, for example, stainless steel, or titanium, or tantalum, or platinum, or palladium or aluminum.

The elongated shaft has, for example, a complementary shape to that of the means (tube) 9 to fit snuggly therein for an efficient transfer of energy.

The elongated shaft 19 may include a knob 21 at a first end. The elongated shaft 19 can include a cage holding means or cage attachment means 23 at a second end. The second end is opposite the first end.

The cage holding means or cage attachment means 23 can include, for example, a threaded extremity or a projection configured to, for example, cooperate with or be received by corresponding sockets or threaded sockets of the cage (for example, a cage as shown on the left in FIG. 7).

A force may be applied to the shaft 19 via, for example, the knob 21, and the energy is transferred from the proximal end to the distal end of the cage holder 1 via both the shaft 19 and the tube 9. The means for transferring energy centrally may thus additionally include the shaft 9.

The cage holder may be part of an instrument kit.

While the invention has been disclosed with reference to certain preferred embodiments, numerous modifications, alterations, and changes to the described embodiments, and equivalents thereof, are possible without departing from the sphere and scope of the invention. The features of any one of the described embodiments may be included in any other of the described embodiments. Accordingly, it is intended that the invention not be limited to the described embodiments and be given the broadest reasonable interpretation in accordance with the language of the appended claims.

The invention claimed is:

1. A cage holder comprising:
   an elongated body comprising a proximal end and a distal end, the elongated body extending from the proximal end to the distal end of the elongated body; and
   a tube configured to transfer energy centrally from a proximal end to a distal end of the cage holder, said tube being at least partially enclosed by the elongated body, the tube extending through the elongated body and from the proximal end to the distal end of the cage holder, the tube comprising or consisting of a first material, the tube configured to transfer energy centrally from the proximal end to the distal end through the elongated body, the tube including an elongated shaft removably held in the cage holder, the elongated shaft including a knob at a first end thereof,
   wherein the elongated body comprises or consists of a second material different from the first material, the first material having a greater material density than a material density of the second material, the tube having a greater rigidity or a lower flexibility than a rigidity or a flexibility of the elongated body, wherein the elongated shaft is removably held inside the tube, and wherein the elongated shaft has a complementary shape to a shape of the tube to fit snuggly inside the tube for a transfer of energy, the elongated shaft being a hollow rod or hollow shaft.

2. The cage holder according to claim 1, wherein the tube is configured to transfer energy centrally through the cage holder in a longitudinal direction of the cage holder from the proximal end of the cage holder to the distal end of the cage holder.

3. The cage holder according to claim 1, wherein the tube configured to transfer energy centrally includes a cage holding or cage attachment system at the distal end of the cage holder.

4. The cage holder according to claim 1, wherein the elongated shaft is configured to movably slide within the cage holder from an outer extremity of the proximal end of the cage holder to an outer extremity of the distal end of the cage holder.

5. The cage holder according to claim 4, wherein the elongated shaft is configured to be received by the tube.

6. The cage holder according to claim 1, wherein the elongated shaft includes a cage holding or cage attachment device at a second end thereof.

7. The cage holder according to claim 1, wherein the distal end of the cage holder is configured to hold or attach a spinal cage.

8. The cage holder according to claim 1, wherein the elongated body includes a handle and the proximal end of the elongated body is located at an end of the handle.

9. The cage holder according to claim 1, wherein the cage holder is a spine cage holder.

10. The cage holder according to claim 1, wherein the tube configured to transfer energy centrally is configured to transfer mechanical energy.

11. The cage holder according to claim 1, wherein the elongated body includes a handle and the proximal end of the elongated body is located at an end of the handle, wherein the elongated shaft includes a cage holding or cage attachment system at a distal end of the elongated shaft.

12. The cage holder according to claim 11, wherein the elongated body includes a sleeve disposed as the distal end of the elongated body.

13. The cage holder according to claim 1, wherein the elongated shaft has a complementary shape to a shape of the tube to fit snuggly inside the tube for a transfer of energy, the elongated shaft being a solid rod elongated shaft.

14. The cage holder according to claim 13, wherein the elongated shaft includes a cage holding or cage attachment system at a distal end of the elongated shaft.

15. The cage holder according to claim 1, wherein the knob is disposed at a proximal end of the elongated shaft and the elongated shaft includes a cage holding or cage attachment system at a distal end of the elongated shaft.

* * * * *